United States Patent

Allard et al.

[11] Patent Number: 6,066,596
[45] Date of Patent: May 23, 2000

[54] HERBICIDAL SYNERGISTIC COMPOSITION, AND METHOD OF CONTROLLING WEEDS

[75] Inventors: Jean Louis Allard, Rheinfelden, Switzerland; Manfred Hudetz, Greensboro, N.C.

[73] Assignee: Novartis Corporation, Summit, N.J.

[21] Appl. No.: 08/729,100

[22] Filed: Oct. 11, 1996

[30] Foreign Application Priority Data

Oct. 13, 1995 [CH] Switzerland .............................. 2910/95

[51] Int. Cl.[7] .................................................. A01N 43/54
[52] U.S. Cl. ............................................................ 504/136
[58] Field of Search .............................................. 504/136

[56] References Cited

U.S. PATENT DOCUMENTS

| | | | |
|---|---|---|---|
| 4,746,353 | 5/1988 | Levitt ............................................ | 71/90 |
| 4,894,085 | 1/1990 | Pews et al. ................................ | 71/105 |
| 5,009,699 | 4/1991 | Brady et al. ................................ | 71/92 |
| 5,104,443 | 4/1992 | Kehne et al. ................................ | 71/92 |
| 5,332,717 | 7/1994 | Lüthy et al. ............................... | 504/242 |

FOREIGN PATENT DOCUMENTS

| | | |
|---|---|---|
| 0342569 | 11/1989 | European Pat. Off. . |
| 9105781 | 5/1991 | WIPO . |

OTHER PUBLICATIONS

The Pesticide Manual (C. Tomlin, 10th Edition) The British Corp Protection Council, Cambridge, pp. 85–87, 211–212, 399, 432–433, 620–621, 649–650, 701–702, 706–707, 828–829, 845–846, 870–871, 873, 874, 1005–1006, 1045–1046 (1996).

*Primary Examiner*—Allen J. Robinson
*Attorney, Agent, or Firm*—William A. Teoli, Jr.; John D. Peabody, III

[57] ABSTRACT

A herbicidal synergistic composition, comprising, besides customary inert formulation auxiliaries, a compound of formula I

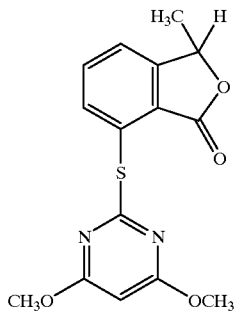

(I)

and a synergistically active amount of at least one active ingredient selected from among the compounds of formula II

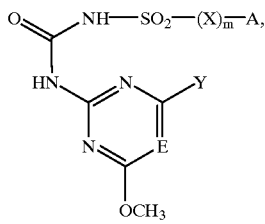

(II)

and of formula III

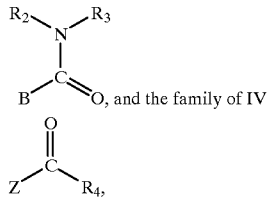

(III)

and the family of IV (IV)

and of formula V

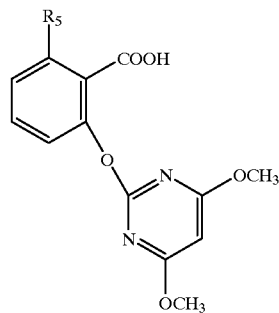

(V)

5 Claims, No Drawings

HERBICIDAL SYNERGISTIC COMPOSITION, AND METHOD OF CONTROLLING WEEDS

The present invention relates to a novel herbicidal synergistic composition which comprises a combination of herbicidally active ingredients suitable for the selective control of weeds in crops of useful plants, for example in rice crops.

The invention furthermore relates to a method of controlling weeds in crops of useful plants, and to the use of this novel composition for this purpose.

The compound of formula I

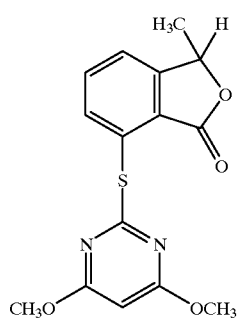

(I)

is herbicidally active, as described in, for example, WO 91/05781.

The following compounds of formulae II to V are also known as herbicides, and some of them are commercially available:

a) Compounds of formula II

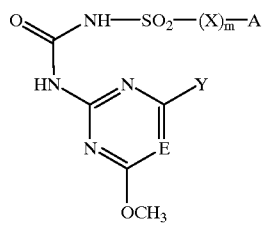

(II)

in which

A is a group 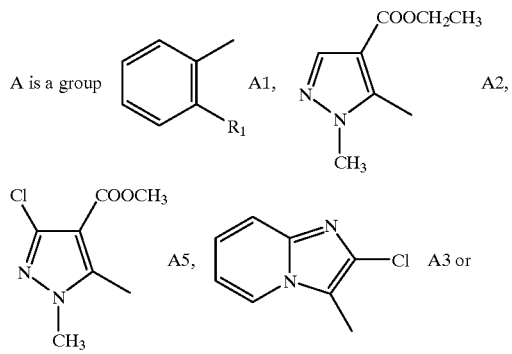

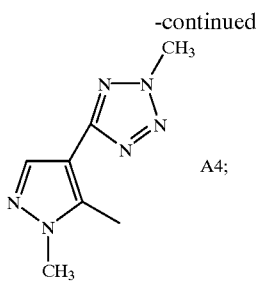

A4;

X is —O—, —CH$_2$— or —NH—;
Y is CH$_3$ or OCH$_3$;
E is CH or N;
R$_1$ is COOCH$_3$, OC$_2$H$_5$, O(CH$_2$)$_2$OCH$_3$, O(CH$_2$)$_2$Cl or

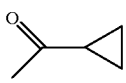

and m in the case of the groups A1 and A4 is the number 0 or 1 and in the case of the groups A2, A5 and A3 the number 0, are known, for example, from The Pesticide Manual, Tenth Edition, The British Crop Protection Council, Cambridge, pages 85, 211, 701, 873 and 1005, and from EP-A-0 342 569, U.S. Pat. No. 5,009,699 and U.S. Pat. No. 4,746,353.

b) Compounds of formula III

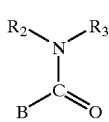

(III)

in which
B is —CH$_2$Cl, —C$_2$H$_5$, —S—CH$_2$CH$_3$,

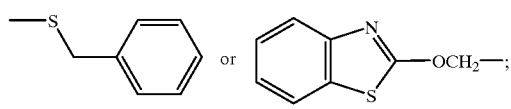

R$_2$ is hydrogen, CH$_3$, C$_2$H5 or —(CH$_2$)$_2$OCH$_2$CH$_2$CH$_3$;
R$_3$ is —CH(CH$_3$)—CH(CH$_3$)$_2$,

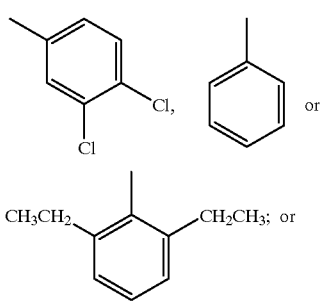

R$_2$ and R$_3$ together are —(CH$_2$)$_6$— are known, for example, from The Pesticide Manual, Tenth Edition, The British Crop Protection Council, Cambridge, pages 399, 649, 706, 828 and 845.

c) Compounds of formula IV

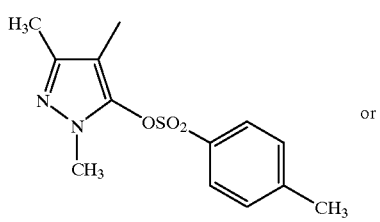

IV in which
Z is

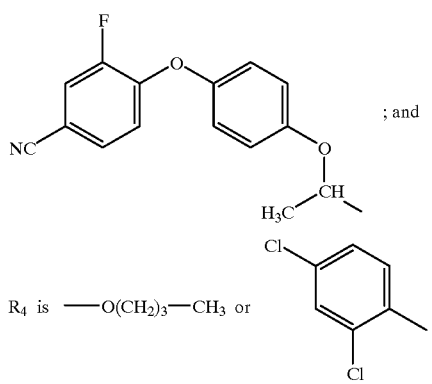

or

; and $R_4$ is —O(CH$_2$)$_3$—CH$_3$ or

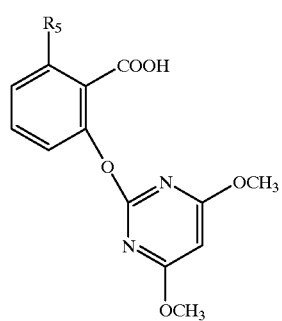

are known, for example, from The Pesticide Manual, Tenth Edition, The British Crop Protection Council, Cambridge, pages 870 and 1045, and from U.S. Pat. No. 4,894,085.

d) Compounds of formula V

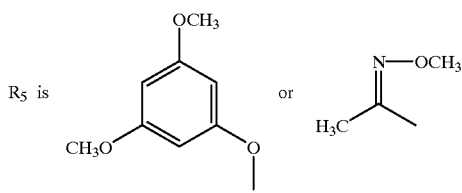

(V)

in which $R_5$ is

or are known, for example, from The Pesticide Manual, Tenth Edition, The British Crop Protection Council, Cambridge, pages 620 and 621.

Surprisingly, it has now emerged that a combination of variable quantities of the active ingredients, i.e. of the active ingredient of formula I with at least one of the active ingredients of formulae II to V displays a synergistic action which is capable of controlling most of the weeds preferably found in crops of useful plants both pre- and post-emergence without seriously harming the useful plant.

In accordance with the present invention, we therefore propose a novel synergistic composition for the selective control of weeds which comprises, as active ingredient, the compound of formula I

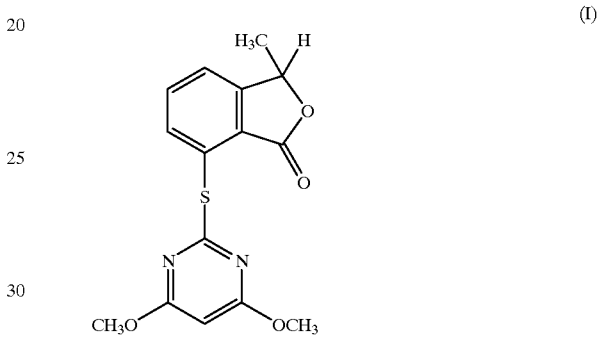

(I)

and a synergistically active amount of at least one active ingredient selected from among the compounds of formula II

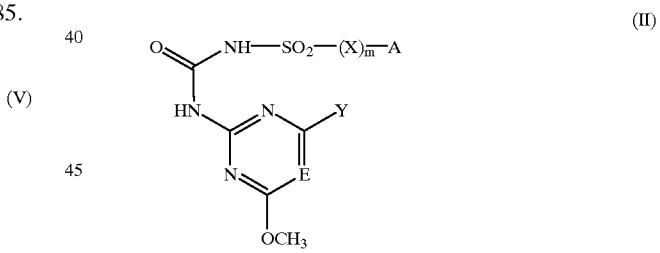

(II)

in which

A is a group 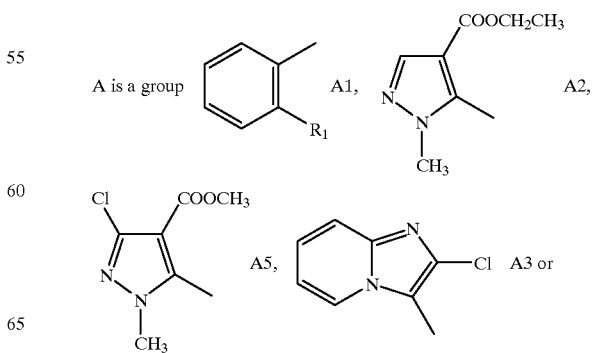

-continued

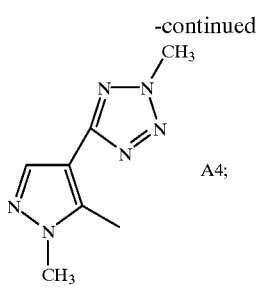

X is —O—, —CH$_2$— or —NH—;
Y is CH$_3$ or OCH$_3$;
E is CH or N;
R$_1$ is COOCH$_3$, OC$_2$H$_5$, O(CH$_2$)$_2$OCH$_3$, O(CH$_2$)$_2$Cl or

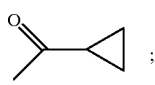;

and m in the case of the groups A1 and A4 is the number 0 or 1 and in the case of the groups A2, A5 and A3 the number 0, and formula III

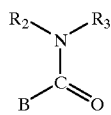 (III)

in which

B is —CH$_2$Cl, —C$_2$H$_5$, —S—CH$_2$CH$_3$,

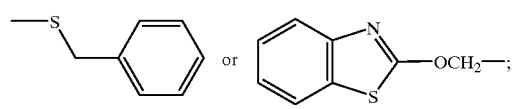;

R$_2$ is hydrogen, CH$_3$, C$_2$H$_5$ or —(CH$_2$)$_2$OCH$_2$CH$_2$CH$_3$;
R$_3$ is —CH(CH$_3$)—CH(CH$_3$)$_2$,

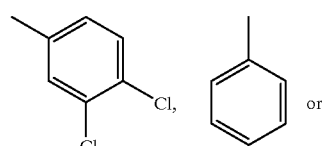 or

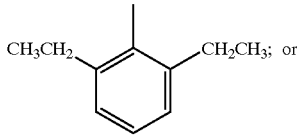

R$_2$ and R$_3$ together are —(CH$_2$)$_6$—; and
of formula IV

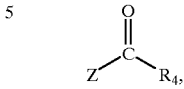 (IV)

in which

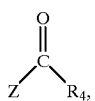 IV

R$_4$ is —O(CH$_2$)$_3$—CH$_3$ or

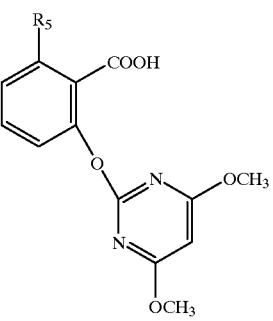; and and of formula V

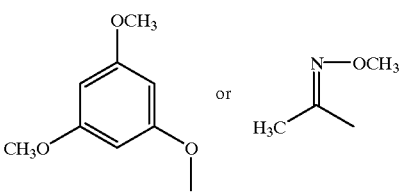 (V)

in which R$_5$ is

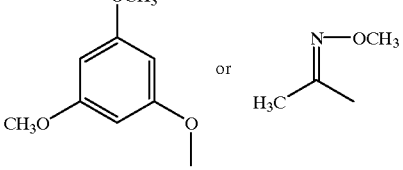

in a mixture with each other, in addition to customary inert formulation auxiliaries. It is highly surprising that the combination of the active ingredient of formula I with at least one of the active ingredients of formulae II to V exceeds the additive action on the weeds to be controlled which is to be expected in principle and thus widens the limits of action of the individual compound in particular in two respects:

On the one hand, the rates of application of the individual compounds I and II to V are lower while the activity remains the same. On the other hand, the composition according to the invention allows a high degree of weed control to be achieved even where the individual substances are no longer agronomically useful in the range of low rates of application.

This results in a considerably widened spectrum of weeds and in an additional increase in selectivity for the crops of useful plants, as is necessary and desirable in the case of unintentional overdosing with active ingredient. Moreover, the composition according to the invention permits more flexibility with subsequent crops while retaining outstanding control of the weeds in useful plants.

The herbicide mixture according to the invention can be used against a large number of agronomically important weeds, such as Stellaria, Nasturtium, Agrostis, Digitaria, Avena, Setaria, Sinapis, Lolium, Solanum, Phaseolus, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Lpomoea, Chrysanthemum, Galium, Viola, Veronica and Heterantera.

The compositions according to the invention are suitable for all application methods conventionally used in agriculture, for example pre-emergence application, post-emergence application and seed dressing.

The herbicide mixture according to the invention is preferably suitable for controlling weeds in crops of useful plants such as cereals, oilseed rape, sugar beet, sugar cane, plantation crops, maize, soya beans and, in particular, rice.

Crops are also to be understood as those which have been made tolerant to herbicides or classes of herbicides by conventional plant-breeding or genetic engineering methods.

The active ingredient combination according to the invention comprises the active ingredient of formula I and one or more of the active ingredients of formulae II to V in any mixing ratio, as a rule with an excess of one over the other component. Preferred mixing ratios between the active ingredient of formula I and the components of formulae II to V are between 1:100 und 100:1, in particular between 1:10 and 10:1.

Preferred compositions according to the invention comprise a compound of formula I

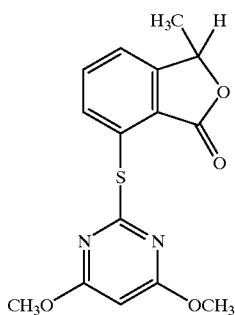
(I)

and a synergistically active amount of either a compound of formula II

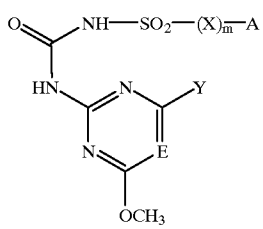
(II)

in which

A is a group

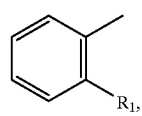
A1

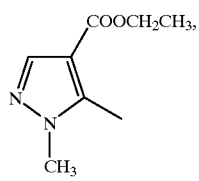
A2

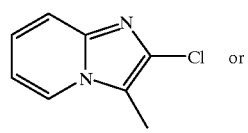
A3 or

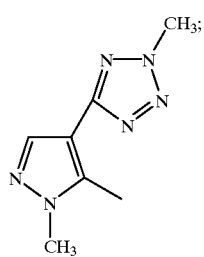
A4

X is —O—, —CH$_2$— or —NH—;

Y is CH$_3$ or OCH$_3$;

E is CH or N;

R$_1$ is COOCH$_3$, OC$_2$H$_5$, O(CH$_2$)$_2$OCH$_3$, O(CH$_2$)$_2$Cl or

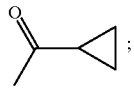;

and m in the case of the groups A1 and A4 is the number 0 or 1 and in the case of the groups A2 and A3 is the number 0; or of formula III

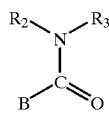
(III)

in which

B is —CH₂Cl, —C₂H₅, —S—CH₂CH₃,

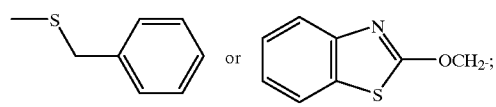

$R_2$ is hydrogen, $CH_3$, $C_2H_5$ or —$(CH_2)_2OCH_2CH_2CH_3$;
$R_3$ is —$CH(CH_3)$—$CH(CH_3)_2$,

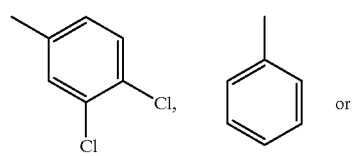 or

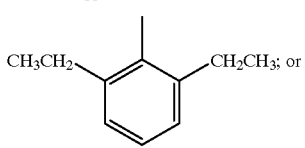

$R_2$ and $R_3$ together are —$(CH_2)_6$—; or
of formula IV

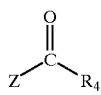
(IV)

in which
Z is

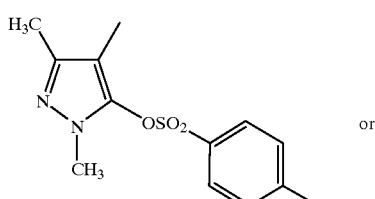 or

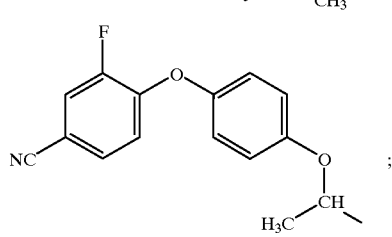;

and $R_4$ is —$O(CH_2)_3$—$CH_3$ or

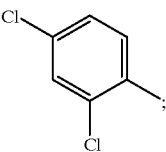;

or of formula V

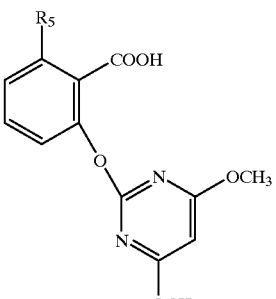
(V)

in which $R_5$ is

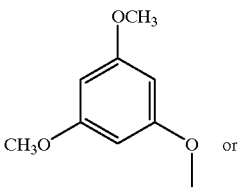 or

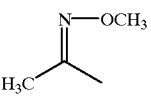

in addition to customary inert formulation auxiliaries.

Preferred compositions according to the invention comprise a compound of formula II in which A is the group

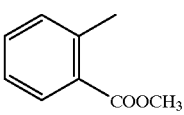

if X is —CH₂— and m is the number 1, or A is a group

A2

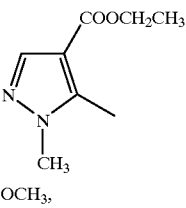 or $OCH_3$,

-continued

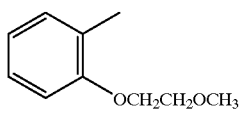

if m is the number zero; and Y is
in addition to the compound of formula I.

Other preferred synergistic compositions are those which comprise a compound of formula III selected from the group consisting of
2-(1,3-benzothiazol-2-yloxy)-N-methylacetanilide,
3',4'-dichloropropionanilide,
2-chloro-2',6'-diethyl-N-(2-propoxyethyl)acetanilide and
S-ethyl azepan-1-carbothioate,
in addition to the compound of formula I.

Especially preferred compositions comprise a synergistically active amount of the active ingredient butyl (R)-2-[4-(4-cyano-2-fluorophenoxy)phenoxy]propionate or of the active ingredient methyl 2-[(4,6-dimethoxypyrimidin-2-yl)oxy]-6-[1-(methoxyimino)ethyl]benzoate or the corresponding carboxylic acid, in addition to the compound of formula I.

A very especially preferred composition comprises a synergistically active amount of the active ingredients 2-chloro-2',6'-diethyl-N-(2-propoxyethyl)acetanilide (pretilachlor) and ethyl 5-(4,6-dimethoxypyrimidin-2-ylcarbamoylsulfamoyl)-1-methylpyrazole-4-carboxylate (NC-311) in addition to the compound of formula I.

Synergistic active ingredient mixtures which have proved very especially effective are combinations of the compound of formula I with the compounds of Tables 1 to 4.

TABLE 1

Preferred compounds of formula II:

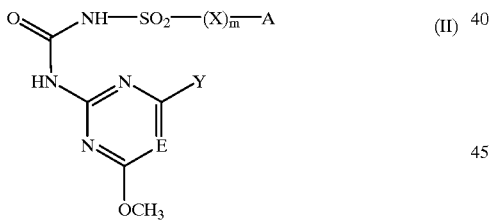

| Comp. No. | A | X | m | E | Y |
|---|---|---|---|---|---|
| 1.1 | ![2-methylphenyl-COOCH3] | CH₂ | 1 | CH | OCH₃ |
| 1.2 | ![pyrazole-COOCH2CH3] | — | 0 | CH | OCH₃ |
| 1.3 | ![2-methylphenyl-OCH2CH2OCH3] | — | 0 | N | OCH₃ |

TABLE 1-continued

Preferred compounds of formula II:

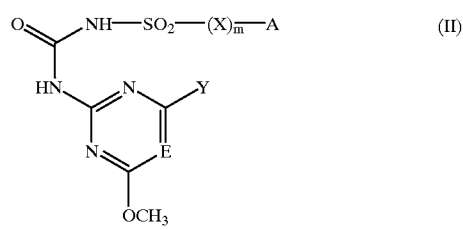

| Comp. No. | A | X | m | E | Y |
|---|---|---|---|---|---|
| 1.4 | ![2-methylphenyl-COOCH3] | — | 0 | N | CH₃ |
| 1.5 | ![2-methylphenyl-OCH2CH2Cl] | — | 0 | N | CH₃ |
| 1.6 | ![imidazopyridine-Cl] | — | 0 | CH | OCH₃ |
| 1.7 | ![2-methylphenyl-OCH2CH3] | O | 1 | CH | OCH₃ |
| 1.8 | ![2-methylphenyl-C(O)-cyclopropyl] | NH | 1 | CH | OCH₃ |
| 1.9 | ![pyrazole-tetrazole] | — | 0 | CH | OCH₃ |
| 1.10 | ![Cl-pyrazole-COOCH3] | — | 0 | CH | OCH₃ |

TABLE 2

Preferred compounds of formula III:

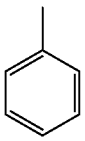

| Comp. No. | B | R₂ | R₃ |
|---|---|---|---|
| 2.1 | 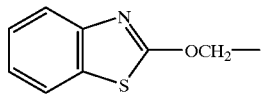 | CH₃ | 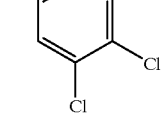 |
| 2.2 | —C₂H₅ | H | 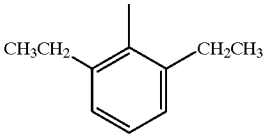 |
| 2.3 | ClCH₂— | —(CH₂)₂OCH₂CH₂CH₃ | 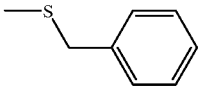 |
| 2.4 | —S—CH₂CH₃ | | —(CH₂)₆— |
| 2.5 | 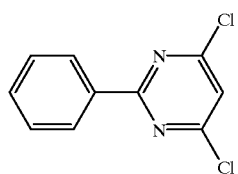 | —C₂H₅ | —CH(CH₃)—CH(CH₃)₂ |

Compounds which are preferably employed are those of formula III, in particular compound No. 2.3, together with the safener of formula VI (VI)

(4,6-dichloro-2-phenylpyrimidine, fenclorim). The safener of formula VI itself is not herbicidally active and cannot potentiate the herbicidal action of the compounds of formula III. The compound of formula VI is known from The Pesticide Manual, Tenth Edition, The British Crop Protection Council, Cambridge, page 432.

TABLE 3

Preferred compounds of formula IV:

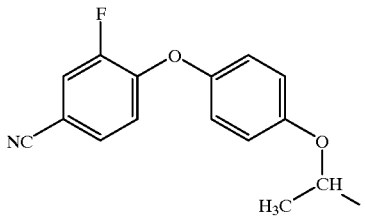

| Comp. No. | Z | $R_4$ |
|---|---|---|
| 3.1 | 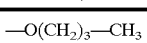 | —O(CH$_2$)$_3$—CH$_3$ |
| 3.2 | 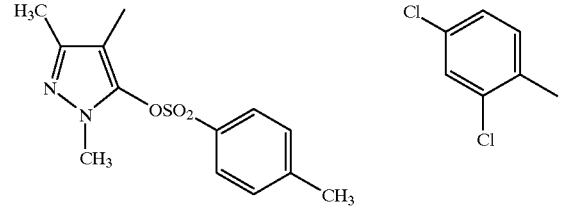 | 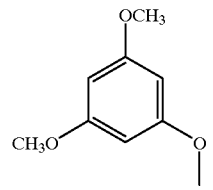 |

TABLE 4

Preferred compounds of formula V:

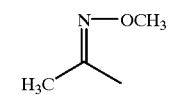

| Comp. No. | $R_5$ |
|---|---|
| 4.1 | (3,5-dimethoxyphenyl group) |
| 4.2 | (N—OCH$_3$ / H$_3$C group) |

The rate of application can vary within wide ranges and depends on the consistency of the soil, the type of application (pre- or post-emergence; seed dressing; application to the seed furrow; no-tillage application and so on), the crop plant, the weeds to be controlled, the climatic conditions prevailing in each case, and other factors determined by type of application, application timing and target crop. In general, the active ingredient mixture according to the invention can be applied at a rate of application of from 0.005 to 6 kg, in particular, 0.02 to 2 kg, of active ingredient mixture/ha.

The composition according to the invention comprises the component of formula I in comparison with the components of formulae II to V in a weight ratio of from 1:1000 to 100:1.

The mixtures of the compound of formula I with the compounds of formulae II to V can be employed in unaltered form, i.e. as obtained from synthesis, but they are preferably processed in the known manner together with the auxiliaries conventionally used in the art of formulation, such as solvents, solid carriers or surfactants, for example to give directly sprayable or dilutable solutions, wettable powders, soluble powders, dusts granules or microcapsules. The methods of application, such as spraying, atomizing, dusting, wetting, scattering or pouring, and the type of composition are selected to suit the intended aims and the prevailing circumsances.

The formulations, i.e. the compositions, preparations or products comprising the active ingredients of formulae I and II to V and, if desired, one or more solid or liquid formulation auxiliaries, are prepared in a manner known per se, for example by intimately mixing and/or grinding the active ingredients with the formulation auxiliaries, for example solvents or solid carriers. Surface-active compounds (surfactants) can, furthermore, additionally be used in the preparation of the formulations.

The following solvents are suitable: aromatic hydrocarbons, preferably the fractions $C_8$ to $C_{12}$, for example xylene mixtures or substituted naphthalenes, phthalic esters, such as dibutyl phthalate or dioctyl phthalate, aliphatic hydrocarbons, such as cyclohexane or paraffins, alcohols and glycols, and also their ethers and esters, such as ethanol, ethylene glycol, ethylene glycol monomethyl ether or ethylene glycol monoethyl ether, ketones, such as cyclohexanone, strongly polar solvents, such as N-methyl-2-pyrrolidone, dimethyl sulfoxide or N,N-dimethylformamide, and unepoxidized or epoxidized vegetable oils, such as epoxidized coconut oil or soya oil; or water.

Solid carriers which are used, for example for dusts and dispersible powders, are, as a rule, ground natural minerals, such as calcite, talc, kaolin, montmorillonite or attapulgite. To improve the physical properties of the formulation, it is also possible to acid highly disperse silica or highly disperse absorptive polymers. Suitable particulate adsorptive carriers for granules are porous types, for example pumice, brick grit, sepiolite or bentonite, and suitable non-absorptive carrier materials are, for example, calcite or sand. Moreover, a large number of pregranulated materials of inorganic or organic nature can be used, such as, in particular, dolomite or comminuted plant residues.

Suitable surface-active compounds are nonionic, cationic and/or anionic surfactants and surfactant mixtures which have good emulsifying, dispersing and wetting properties, depending on the nature of the active ingredient of formula I to be formulated.

Suitable anionic surfactants can be both so-called water-soluble soaps and water-soluble synthetic surface-active compounds.

Soaps which may be mentioned are the alkali metal, alkaline earth metal or substituted or unsubstituted ammonium salts of higher fatty acids ($C_{10}$–$C_{22}$), for example the sodium or potassium salt of oleic or stearic acid, or of natural fatty acid mixtures which can be obtained, for example, from coconut or tallow oil. The fatty acid methyltaurine salts may furthermore be mentioned.

However, so-called synthetic surfactants, in particular fatty alcohol sulforates, fatty alcohol sulfates, sulfonated benzimidazole derivatives or alkylarylsulfonates, are used more frequently.

As a rule, the fatty alcohol sulfonates or fatty alcohol sulfates are in the form of alkali metal, alkali earth metal or substituted or unsubstituted ammonium salts and have an alkyl radical of 8 to 22 carbon atoms, alkyl also embracing the alkyl moiety of acyl radicals, e.g. the sodium or calcium salt of lignosulfonic acid, of the dodecylsulfuric ester or of a fatty alcohol sulfate mixture prepared from natural fatty acids. They also include the salts of the sulfuric esters and sulfonic acids of fatty alcohol/ethylene oxide adducts. The sulfonated benzimidazole derivatives comprise preferably 2 sulfo groups and a fatty acid radical having 8–22 carbon atoms. Alkylarylsulfonates are, for example, the sodium, calcium or triethanolamine salts of dodecylbenzenesulfonic acid, of dibutylnaphthalenesulfonic acid, or of a naphthalenesulfonic acid/formaldehyde condensate.

Corresponding phosphates, for example salts of the phosphoric ester of a p-nonylphenol-(4–14)ethylene oxide adduct, or phospholipids, are furthermore also suitable.

Suitable nonionic surfactants are mainly polyglycol ether derivatives of aliphatic or cycloaliphatic alcohols, of saturated or unsaturated fatty acids and of alkylphenols which can have 3 to 30 glycol ether groups and 8 to 20 carbon atoms in the (aliphatic) hydrocarbon radical and 6 to 18 carbon atoms in the alkyl radical of the alkylphenols.

Other suitable nonionic surfactants are the water-soluble polyethylene oxide adducts with polypropylene glycol, ethylenediaminopolypropylene glycol and alkylpolypropylene glycol having 1 to 10 carbon atoms in the alkyl chain which contain 20 to 250 ethylene glycol ether groups and 10 to 100 propylene glycol ether groups. The abovementioned compounds normally contain 1 to 5 ethylene glycol units per propylene glycol unit.

Examples of nonionic surfactants which may be mentioned are nonylphenolpolyethoxy-ethanols, castor oil polyglycol ethers, polypropylene/polyethylene oxide adducts, tributylphenoxypolyethoxyethanol, polyethylene glycol and octylphenoxypolyethoxyethanol.

Substances which are also suitable are fatty acid esters of polyoxyethylene sorbitan, such as polyoxyethylene sorbitan trioleate.

The cationic surfactants are mainly quaternary ammonium salts which have, as N substituents, at least one alkyl radical having 8 to 22 carbon atoms and, as further substituents, lower, free or halogenated alkyl, benzyl or lower hydroxyalkyl radicals. The salts exist preferably as halides, methylsulfates or ethylsulfates, for example stearyltrimethylammonium chloride or benzyldi(2-chloroethyl)ethylammonium bromide.

The surfactants conventionally used in the art of formulation which can also be used in the compositions according to the invention are described, inter alia, in "Mc Cutcheon's Detergents and Emulsifiers Annual" MC Publishing Corp., Ridgewood N.J., 1981, Stache, H., "Tensid-Taschenbuch" [Surfactants Guide], Carl Hanser Verlag, Munich/Vienna, 1981 and M. and J. Ash, "Encyclopedia of Surfactants", Vol I–III, Chemical Publishing Co., New York, 1980–81.

As a rule, the herbicidal formulations comprise 0.1 to 99% by weight, in particular 0.1 to 95% by weight, of active ingredient mixture composed of the compound of formula I and the compounds of formulae II to V, 1 to 99.9% by weight of a solid or liquid formulation auxiliary at 0 to 25% by weight, in particular 0.1 to 25% by weight, of a surfactant.

While concentrated compositions are normally preferred as commercially available goods, the end user uses, as a rule, dilute compositions.

The compositions can also comprise other additives such as stabilizers, for example unepoxidized or epoxidized vegetable oils (epoxidized coconut oil, rapeseed oil or soya oil), antifoams, for example silicone oil, preservatives, viscosity regulators, binders, tackifiers and also fertilizers or other active ingredients.

In particular, preferred formulations are composed as follows: (%=percent by weight)

| Dusts: | |
|---|---|
| Active ingredient mixture: | 0.1 to 10%, preferably 0.1 to 5% |
| Solid carrier: | 99.9 bis 90%, preferably 99.9 to 99% |
| Suspension concentrate: | |
| Active ingredient mixture: | 5 to 75%, preferably 10 to 50% |
| Water: | 94 bis 24%, preferably 88 to 30% |
| Surfactant: | 1 to 40%, preferably 2 to 30% |
| Wettable powders: | |
| Active ingredient mixture: | 0.5 to 90%, preferably 1 to 80% |
| Surfactant: | 0.5 to 20%, preferably 1 to 15% |
| Solid carrier: | 5 to 95%, preferably 15 to 90% |
| Granules: | |
| Active ingredient mixture: | 0.1 to 30%, preferably 0.1 to 15% |
| Solid carrier: | 99.5 to 70%, preferably 97 to 85% |

The examples which follow illustrate the invention in greater detail without imposing any limitation thereon.
Formulation Examples of Mixtures of Compounds of Formulae I and II to V (%=Percent by Weight)

| F1. solutions | a) | b) | c) | d) |
|---|---|---|---|---|
| Active ingredient mixture | 5% | 10% | 50% | 90% |
| 1-methoxy-3-(3-methoxy-propoxy)propane | — | 20% | 20% | — |
| Polyethylene glycol MW 400 | 20% | 10% | — | — |
| N-methyl-2-pyrrolidone | — | — | 30% | 10% |
| Mixture of aromatic hydrocarbons $C_9$–$C_{12}$ | 75% | 60% | — | — |

The solutions are suitable for use in the form of microdrops.

| F2. Wettable powders | a) | b) | c) | d) |
|---|---|---|---|---|
| Active ingredient mixture | 5% | 25% | 50% | 80% |
| Sodium lignosulfonate | 4% | — | 3% | — |
| Sodium lauryl sulfate | 2% | 3% | — | 4% |
| Sodium diisobutylnaphthalene-sulphonate | — | 6% | 5% | 6% |
| Octylphenol polyglycol ether (7–8 mol of EO) | — | 1% | 2% | — |
| Highly disperse silica | 1% | 3% | 5% | 10% |
| Kaolin | 88% | 62% | 35% | — |

The active ingredient is mixed thoroughly with the additives and ground thoroughly in a suitable mill. This gives wettable powders which can be diluted with water to give suspensions of any desired concentration.

| F3. Coated granules | a) | b) | c) |
|---|---|---|---|
| Active ingredient mixture | 0.1% | 5% | 15% |
| Highly disperse silica | 0.9% | 2% | 2% |
| Inorganic carrier (Ø 0.1–1 mm), for example $CaCO_3$ or $SiO_2$ | 99.0% | 93% | 83% |

The active ingredient is dissolved in methylene chloride, sprayed onto the carrier, and the solvent is subsequently evaporated in vacuo.

| F4. Coated granules | a) | b) | c) |
|---|---|---|---|
| Active ingredient mixture | 0.1% | 5% | 15% |
| Polyethylene glycol MW 200 | 1.0% | 2% | 3% |
| Highly disperse silica | 0.9% | 1% | 2% |
| Inorganic carrier (Ø 0.1–1 mm) for example $CaCO_3$ or $SiO_2$ | 98.0% | 92% | 80% |

In a mixer, the finely ground active ingredient is applied uniformly to the carrier which has been moistened with polyethylene glycol. This gives dust-free coated granules.

| F5. Extruder granules | a) | b) | c) | d) |
|---|---|---|---|---|
| Active ingredient mixture | 0.1% | 3% | 5% | 15% |
| Sodium lignosulfonate | 1.5% | 2% | 3% | 4% |
| Carboxymethylcellulose | 1.4% | 2% | 2% | 2% |
| Kaolin | 97.0% | 93% | 90% | 79% |

The active ingredient is mixed with the additives, and the mixture is ground and moistened with water. This mixture is extruded and subsequently dried in a stream of air.

| F6. Dusts | a) | b) | c) |
|---|---|---|---|
| Active ingredient mixture | 0.1% | 1% | 5% |
| Talc | 39.9% | 49% | 35% |
| Kaolin | 60.0% | 50% | 60% |

Ready-to-use dusts are obtained by mixing the active ingredient with carriers and grinding the mixture on a suitable mill.

| F7. Suspension concentrates | a) | b) | c) | d) |
|---|---|---|---|---|
| Active ingredient mixture | 3% | 10% | 25% | 50% |
| Ethylene glycol | 5% | 5% | 5% | 5% |
| Nonylphenol polyglycol ether (15 mol of EO) | — | 1% | 2% | — |
| Sodium lignosulfonate | 3% | 3% | 4% | 5% |
| Carboxymethylcellulose | 1% | 1% | 1% | 1% |
| 37% aqueous formaldehyde solution | 0.2% | 0.2% | 0.2% | 0.2% |
| Silicone oil emulsion | 0.8% | 0.8% | 0.8% | 0.8% |
| Water | 87% | 79% | 62% | 38% |

The finely ground active ingredient is mixed intimately with the additives. This gives a suspension concentrate from which suspensions of any desired concentration can be prepared by diluting it with water.

Frequently, it is more practical to formulate the active ingredient of formula I and the component, or components, of formulae II to V individually and then to combine them in the applicator in the water in the desired mixing ratio shortly before application to give a "tank mix".

BIOLOGICAL EXAMPLES

A synergistic effect is always present when the activity of the active ingredient combination I and II, and/or III, and/or IV and/or V exceeds the total of the activity of the active ingredients applied singly.

The expected herbicidal activity Ae for a given combination of two herbicides can be calculated as follows (cf. COLBY, S. R., "Calculating synergistic and antagonistic response of herbicide combinations", Weeds 15, pages 20–22, 1967):

$$Ae = X + [Y \cdot (100-X)/100]$$

In this formula,

X=percent herbicidal activity in the treatment with the compound of formula I using a rate of application of p kg per hectare in comparison with untreated control (=0%).

Y=percent herbicidal activity in the treatment with the compound of formulae II to V using a rate of application of q kg per hectare in comparison with untreated control.

Ae=expected herbicidal activity (percent herbicidal activity comparison with the untreated control) after treatment with the compounds of formulae I and II to V at a rate of application of p+q kg of active ingredient per hectare.

If the activity actually observed exceeds the expected value Ae, synergism is present. Recognition is given by those skilled in the art to synergistically increased activities of herbicide combinations from a herbicidal activity of 0–50% (expected value) to 70–100% herbicidal activity (observed), and from 90–95% herbicidal activity (expected value) to 95–100% herbicidal activity (observed).

The synergistic effect of the combinations of the active ingredient of formula I with at least one of the active ingredients of formulae II to V is demonstrated in the following examples.

Example B1

Post-Emergence Experiment

The test plants are grown in plastic pots under greenhouse conditions until they have reached the 2–3 leaf stage. The culture substrate used is a standard soil. The herbicides alone and in the form of a mixture are applied to the test plants in the 2–3 leaf stage. Application is effected in the form of an aqueous suspension of the test substance (Formulation F7, c)) in 500 l of water/ha. The rates of application depend on the optimal dosage rates determined under field conditions and greenhouse conditions. After 21 days, the experiments are evaluated (% activity, 100%=plant dead, 0%=no phytotoxic activity).

In this experiment, the combinations of the active ingredient of formula I with the active ingredients of formulae II to V show a synergistic activity.

Example B2

Herbicidal Activity in Paddy Rice (Transplanted)

The test plants are sown or planted in standard soil in shallow plastic containers under greenhouse conditions. The containers are then filled with water to soil level. After 3 days, the water level is raised by 2 cm, and the test substances are applied in the form of an aqueous suspension (Formulation Example F7, c)) by the run-in method (application into the water). The test plants are then grown on in the greenhouse under optimal conditions. 25 days after application, the test is evaluated using a % scale (100%= complete damage, 0%=no activity). Scores from 70% to 100% (in particular 80% to 100%) denote a good to very good herbicidal activity, scores from 0% to 30% (in particular 0% to 20%) show that the crop plant tolerance is good to very good.

Test plants: transplanted rice, Sagittaria pygmaea, Scirpus juncoides and Heterantera.

In this experiment, again, the combinations of the active ingredient of formula I with the active ingredients of formulae II to V show a synergistic activity.

Examples of the synergistic efficacy of the combinations of the active ingredients of formula I with the active ingredients of formulae II, III and IV are shown in Tables B1, B2 and B3.

TABLE B1

Experiments in transplanted rice with *sagittaria pygmaea*, using the run-in method

| Comp. No. | Rate of application [g or active ingredient/ha] | Crop plant transplanted rice | Weed *Sagittaria pygm.* | Ae [expected value] |
|---|---|---|---|---|
| I | 80 | 0 | 0 | |
| 1.1 | 30 | 0 | 80 | |
| I + 1.1 | 60 + 30 | 0 | 94 | 80 |
| I | 120 | 0 | 0 | |
| 1.1 | 30 | 0 | 80 | |
| I + 1.1 | 120 + 30 | 0 | 90 | 80 |
| I | 240 | 0 | 0 | |
| 1.1 | 8 | 0 | 70 | |
| I + 1.1 | 240 + 8 | 0 | 90 | 70 |
| I | 240 | 0 | 0 | |

TABLE B1-continued

Experiments in transplanted rice with *sagittaria pygmaea*, using the run-in method

| Comp. No. | Rate of application [g or active ingredient/ha] | Crop plant transplanted rice | Weed *Sagittaria pygm.* | Ae [expected value] |
|---|---|---|---|---|
| 1.1 | 15 | 0 | 80 | |
| I + 1.1 | 240 + 15 | 0 | 90 | 80 |
| I | 240 | 0 | 0 | |
| 1.1 | 30 | 0 | 80 | |
| I + 1.1 | 240 + 30 | 0 | 90 | 80 |
| I | 60 | 0 | 0 | |
| 1.3 | 12 | 0 | 75 | |
| I + 1.3 | 60 + 12 | 0 | 92 | 75 |
| I | 60 | 0 | 0 | |
| 1.3 | 24 | 15 | 94 | |
| I + 1.3 | 60 + 24 | 15 | 98 | 94 |
| I | 120 | 0 | 0 | |
| 1.3 | 12 | 0 | 75 | |
| I + 1.3 | 120 + 12 | 0 | 94 | 75 |
| I | 240 | 0 | 0 | |
| 1.3 | 6 | 0 | 70 | |
| I + 1.3 | 240 + 6 | 0 | 92 | 70 |
| I | 240 | 0 | 0 | |
| 1.3 | 12 | 0 | 75 | |
| I + 1.3 | 240 + 12 | 5 | 94 | 75 |
| I | 120 | 0 | 0 | |
| 2.1 | 1000 | 0 | 0 | |
| I + 2.1 | 120 + 1000 | 0 | 50 | 0 |
| I | 240 | 0 | 0 | |
| 2.1 | 500 | 0 | 0 | |
| I + 2.1 | 240 + 500 | 5 | 70 | 0 |
| I | 240 | 0 | 0 | |
| 2.1 | 1000 | 0 | 0 | |
| I + 2.1 | 240 + 1000 | 25 | 85 | 0 |
| I | 120 | 0 | 0 | |
| 3.1 | 125 | 0 | 0 | |
| I + 3.1 | 120 + 125 | 0 | 50 | 0 |
| I | 120 | 0 | 0 | |
| 3.1 | 250 | 0 | 0 | |
| I + 3.1 | 120 + 250 | 0 | 50 | 0 |
| I | 240 | 0 | 0 | |
| 3.1 | 250 | 0 | 0 | |
| I + 3.1 | 240 + 250 | 0 | 60 | 0 |
| I | 60 | 0 | 0 | |
| 1.2 | 30 | 0 | 0 | |
| I + 1.2 | 60 + 30 | 0 | 90 | 0 |
| I | 120 | 0 | 0 | |
| 1.2 | 30 | 0 | 20 | |
| I + 1.2 | 120 + 30 | 0 | 92 | 20 |
| I | 240 | 0 | 0 | |
| 1.2 | 30 | 0 | 20 | |
| I + 1.2 | 240 + 30 | 0 | 96 | 20 |
| I | 120 | 0 | 0 | |
| 2.2 | 1000 | 0 | 0 | |
| I + 2.2 | 120 + 1000 | 0 | 50 | 0 |
| I | 240 | 0 | 0 | |
| 2.2 | 500 | 0 | 0 | |
| I + 2.2 | 240 + 500 | 0 | 80 | 0 |
| I | 240 | 0 | 0 | |
| 2.2 | 1000 | 0 | 0 | |
| I + 22 | 240 + 1000 | 15 | 80 | 0 |
| I | 60 | 0 | 0 | |
| 2.3 | 250 | 0 | 25 | |
| I + 2.3 | 60 + 250 | 0 | 60 | 25 |
| I | 240 | 0 | 0 | |
| 2.3 | 500 | 0 | 50 | |
| I + 2.3 | 240 + 500 | 0 | 70 | 50 |
| I | 60 | 0 | 0 | |
| 2.3 | 375 | 0 | 55 | |
| VI | 125 | 0 | 0 | |
| I + 2.3 + VI | 60 + 375 + 125 | 0 | 70 | 55 |
| I | 240 | 0 | 0 | |
| 2.3 | 375 | 0 | 55 | |
| VI | 125 | 0 | 0 | |
| I + 2.3 + VI | 240 + 375 + 125 | 10 | 90 | 55 |

TABLE 2B

Experiments in transplanted rice with *Scirpus juncoides*, using the run-in method

| Comp. No. | Rate of application [g or active ingredient/ha] | Crop plant transplanted rice | Weed Scirpus junc. | Ae [expected value] |
|---|---|---|---|---|
| I | 60 | 0 | 0 | |
| 2.1 | 125 | 0 | 0 | |
| I + 2.1 | 60 + 125 | 0 | 92 | 0 |
| I | 60 | 0 | 0 | |
| 2.1 | 250 | 0 | 65 | |
| I + 2.1 | 60 + 250 | 0 | 92 | 65 |
| I | 60 | 0 | 0 | |
| 2.1 | 500 | 0 | 94 | |
| I + 2.1 | 60 + 500 | 0 | 99 | 94 |
| I | 60 | 0 | 0 | |
| 3.1 | 125 | 0 | 0 | |
| I + 3.1 | 60 + 125 | 0 | 50 | 0 |
| I | 60 | 0 | 0 | |
| 3.1 | 250 | 0 | 0 | |
| I + 3.1 | 60 + 250 | 0 | 90 | 0 |
| I | 120 | 0 | 50 | |
| 3.1 | 250 | 0 | 0 | |
| I + 3.1 | 120 + 250 | 0 | 94 | 50 |
| I | 60 | 0 | 0 | |
| 1.2 | 15 | 0 | 0 | |
| I + 1.2 | 60 + 15 | 0 | 90 | 0 |
| I | 60 | 0 | 0 | |
| 1.2 | 30 | 0 | 20 | |
| I + 1.2 | 60 + 30 | 0 | 96 | 20 |
| I | 120 | 0 | 50 | |
| 1.2 | 15 | 0 | 0 | |
| I + 1.2 | 120 + 15 | 0 | 96 | 50 |
| I | 120 | 0 | 50 | |
| 1.2 | 30 | 0 | 20 | |
| I + 1.2 | 120 + 30 | 0 | 97 | 60 |
| I | 60 | 0 | 0 | |
| 2.2 | 1000 | 0 | 35 | |
| I + 2.2 | 60 + 1000 | 0 | 92 | 35 |
| I | 120 | 0 | 50 | |
| 2.2 | 500 | 0 | 0 | |
| I + 2.2 | 120 + 50 | 0 | 85 | 50 |
| I | 120 | 0 | 50 | |
| 2.2 | 1000 | 0 | 35 | |
| I + 2.2 | 120 + 1000 | 0 | 96 | 68 |
| I | 240 | 0 | 92 | |
| 2.2 | 500 | 0 | 0 | |
| I + 2.2 | 240 + 500 | 0 | 96 | 92 |

TABLE B3

Experiments in transplanted rice with Heterantera, using the run-in method

| Comp. No. | Rate of application [g or active ingredient/ha] | Crop plant transplanted rice | Weed Hete-rantera | Ae [expected value] |
|---|---|---|---|---|
| I | 60 | 0 | 0 | |
| 1.1 | 30 | 0 | 75 | |
| I + 1.1 | 60 + 30 | 0 | 96 | 75 |
| I | 120 | 0 | 0 | |
| 1.1 | 30 | 0 | 75 | |
| I + 1.1 | 120 + 30 | 0 | 90 | 75 |
| I | 60 | 0 | 0 | |
| 2.1 | 500 | 0 | 40 | |
| I + 2.1 | 60 + 500 | 0 | 70 | 40 |
| I | 120 | 0 | 0 | |
| 2.1 | 500 | 0 | 40 | |
| I + 2.1 | 120 + 500 | 0 | 70 | 40 |
| I | 120 | 0 | 0 | |
| 2.1 | 1000 | 0 | 50 | |
| I + 2.1 | 120 + 1000 | 0 | 85 | 50 |
| I | 60 | 0 | 0 | |
| 2.3 | 60 | 0 | 0 | |
| I + 2.3 | 60 + 60 | 0 | 55 | 0 |
| I | 60 | 0 | 0 | |
| 2.3 | 375 | 0 | 80 | |
| VI | 125 | 0 | 0 | |
| I + 2.3 + VI | 60 + 375 + 125 | 0 | 94 | 80 |
| I | 120 | 0 | 0 | |
| 2.3 | 375 | 0 | 80 | |
| VI | 125 | 0 | 0 | |
| I + 2.3 + VI | 120 + 375 + 125 | 0 | 94 | 80 |
| I | 120 | 0 | 0 | |
| 3.1 | 125 | 0 | 0 | |
| I + 3.1 | 120 + 125 | 0 | 50 | 0 |
| I | 120 | 0 | 0 | |
| 3.1 | 250 | 0 | 0 | |
| I + 3.1 | 120 + 250 | 0 | 60 | 0 |
| I | 120 | 0 | 0 | |
| 1.2 | 8 | 0 | 0 | |
| I + 1.2 | 120 + 8 | 0 | 55 | 0 |
| I | 120 | 0 | 0 | |
| 1.2 | 15 | 0 | 0 | |
| I + 1.2 | 120 + 15 | 0 | 50 | 0 |
| I | 120 | 0 | 0 | |
| 1.2 | 30 | 0 | 0 | |
| I + 1.2 | 120 + 30 | 0 | 60 | 0 |
| I | 240 | 0 | 70 | |
| 2.2 | 1000 | 0 | 0 | |
| I + 2.2 | 240 + 1000 | 15 | 85 | 70 |

Example B3

Herbicidal Activity in Dry-Seeded Flooded Rice

The test plants are sown in standard soil in shallow plastic containers under greenhouse conditions and grown on for 2 to 3 weeks in the greenhouse under optimal conditions. The test substances are subsequently applied to the test plants in the form of a aqueous suspension (Formulation Example F7, c)). After application, the shallow containers are flooded with water. 7 and 28 days after application, the experiment is evaluated using a % scale (100%=complete damage, 0%=no activity). Scores from 70% to 100% (in particular 80% to 100%) denote a good to very good herbicidal activity, scores from 0% to 30% (in particular 0% to 20%) show that the crop plant tolerance is good to very good. Test plants: seeded rice, Echinochloa, Scirpus, Monochoria, Sagittaria, Cyperus s. and Eleocharis.

In this experiment, again, the combinations of the active ingredients of formula I with active ingredients of formulae II to V show a synergistic activity.

What is claimed is:

1. A herbicidal synergistic composition, comprising, customary inert formulation auxiliaries, and synergistic herbicidal effective amounts of the compound of formula I

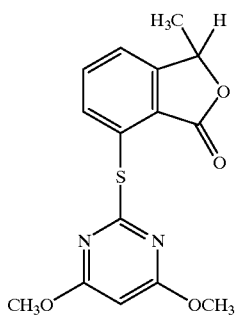

(I)

and the compound ethyl 5-(4,6,-dimethoxypyrimidin-2-yl-carbamoylsulfamoyl)-1-methylpyrazole-4-carboxylate.

2. A herbicidal composition according to claim 1, which comprises the compound of formula I relative to the compound ethyl 5-(4,6,-dimethoxypyrimidin-2-yl-carbamoylsulfamoyl)-1-methylpyrazole-4-carboxylate in a weight ratio of 1:1000 to 100:1.

3. A herbicidal composition according to claim 2, wherein said weight ratio is 1:8 to 40:1.

4. A method of controlling undesirable vegetation in crops of rice plants, which comprises applying a synergistic herbicidally effective amount of a composition according to claim 1 to the rice plant or its environment.

5. A method according to claim 4, wherein the crops of rice plants are treated with the composition mentioned at rates of application which correspond to a total amount of 0.005 to 6 kg of active ingredient per hectare.

* * * * *